(12) United States Patent
Melvin

(10) Patent No.: US 7,081,084 B2
(45) Date of Patent: Jul. 25, 2006

(54) MODULAR POWER SYSTEM AND METHOD FOR A HEART WALL ACTUATION SYSTEM FOR THE NATURAL HEART

(75) Inventor: David Boyd Melvin, Loveland, OH (US)

(73) Assignee: University of Cincinnati, Cincinnati, OH (US)

( * ) Notice: Subject to any disclaimer, the term of this patent is extended or adjusted under 35 U.S.C. 154(b) by 147 days.

(21) Appl. No.: 10/196,439

(22) Filed: Jul. 16, 2002

(65) Prior Publication Data

US 2004/0015039 A1 Jan. 22, 2004

(51) Int. Cl.
*A61M 1/12* (2006.01)
(52) U.S. Cl. .......................................... 600/16; 623/3.1
(58) Field of Classification Search ................ 600/16, 600/17, 18; 607/3, 9; 623/3.1, 3.12
See application file for complete search history.

(56) References Cited

U.S. PATENT DOCUMENTS

| | | | |
|---|---|---|---|
| 2,826,193 A | 3/1958 | Vineberg | |
| 3,053,249 A | 9/1962 | Smith | |
| 3,455,298 A | 7/1969 | Anstadt | |
| 3,513,836 A | 5/1970 | Sausse | |
| 3,590,815 A | 7/1971 | Schiff | |
| 3,613,672 A | 10/1971 | Schiff | |
| 3,668,708 A | 6/1972 | Tindal | |
| 3,713,439 A | 1/1973 | Cabezudo | |
| 3,791,388 A | 2/1974 | Hunter et al. | |
| 3,827,426 A | 8/1974 | Paige et al. | |
| 3,835,864 A * | 9/1974 | Rasor et al. ................. | 607/36 |
| 3,983,863 A | 10/1976 | Janke et al. | |
| 4,192,293 A | 3/1980 | Asrican | |

(Continued)

FOREIGN PATENT DOCUMENTS

EP 119357 9/1984

(Continued)

OTHER PUBLICATIONS

Melvin, D.B.; Conkle, D.; Roberts, A; Stinson, E.;, "*Cardiac Performance and Myocardial Contractility After Experimental Mechanical Ventricular Assistance*", J. Thoracic and Cardiovascular Surgery vol. 65, No. 6, Jun. 1973.

(Continued)

*Primary Examiner*—Kennedy Schaetzle
(74) *Attorney, Agent, or Firm*—Wood Herron & Evans, LLP

(57) ABSTRACT

An actuation system for assisting the operation of a natural heart is disclosed. The actuation system includes a framework for interfacing with the natural heart and a power system that can be coupled to the framework. The framework includes an internal framework element and an external framework element. The power system is configured to engage an exterior surface of the heart wall, and includes an actuator mechanism for exerting force on the heart wall, a driving mechanism for actuating the actuator mechanism, a transmission mechanism coupled between the actuator mechanism and the driving mechanism for transmitting power to the actuator mechanism, and a carrier device coupled between the actuator mechanism and the driving mechanism and configured for housing the transmission mechanism. The modular power system is configured for being freely exchanged and replaced in the actuation system while leaving the framework elements in place and generally undisturbed. A guide structure such as a wire or tube can also be included for guiding or advancing the power system to its position adjacent to the heart surface.

30 Claims, 4 Drawing Sheets

U.S. PATENT DOCUMENTS

| | | | |
|---|---|---|---|
| 4,536,893 A | 8/1985 | Parravicini | |
| 4,621,617 A | 11/1986 | Sharma | |
| 4,690,134 A | 9/1987 | Snyders | |
| 4,809,676 A | 3/1989 | Freeman | |
| 4,846,831 A | 7/1989 | Skillin | |
| 4,904,255 A | 2/1990 | Chareire et al. | |
| 4,936,857 A | 6/1990 | Kulik | |
| 4,957,477 A | 9/1990 | Lundback | |
| 5,109,843 A | 5/1992 | Melvin et al. | |
| 5,119,804 A | 6/1992 | Anstadt | |
| 5,131,905 A | 7/1992 | Grooters | |
| 5,139,517 A | 8/1992 | Corral | |
| 5,169,381 A | 12/1992 | Snyders | |
| 5,192,314 A | 3/1993 | Daskalakis | |
| 5,201,880 A | 4/1993 | Wright et al. | |
| 5,256,132 A | 10/1993 | Snyders | |
| 5,258,021 A | 11/1993 | Duran | |
| 5,334,217 A | 8/1994 | Das | |
| 5,345,949 A | 9/1994 | Shlain | |
| 5,358,519 A | 10/1994 | Grandjean | |
| 5,370,685 A | 12/1994 | Stevens | |
| 5,383,840 A | 1/1995 | Heilman et al. | |
| 5,385,528 A | 1/1995 | Wilk | |
| 5,484,391 A | 1/1996 | Buckman, Jr. et al. | |
| 5,487,760 A | 1/1996 | Villafana | |
| 5,533,958 A | 7/1996 | Wilk | |
| 5,571,176 A | 11/1996 | Taheri | |
| 5,593,424 A | 1/1997 | Northrup III | |
| 5,655,548 A | 8/1997 | Nelson et al. | |
| 5,702,343 A | 12/1997 | Alferness | |
| 5,709,695 A | 1/1998 | Northrup, III | |
| 5,713,954 A | 2/1998 | Rosenberg et al. | |
| 5,738,626 A | 4/1998 | Jarvik | |
| 5,738,627 A | 4/1998 | Kovacs et al. | |
| 5,749,883 A | 5/1998 | Halpern | |
| 5,800,528 A | 9/1998 | Lederman et al. | |
| 5,824,071 A | 10/1998 | Nelson et al. | |
| 5,910,124 A | 6/1999 | Rubin | |
| 5,957,977 A | 9/1999 | Melvin | |
| 5,961,440 A | 10/1999 | Schweich, Jr. et al. | |
| 6,019,722 A | 2/2000 | Spence et al. | |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,077,214 A | 6/2000 | Mortier et al. | |
| 6,085,754 A | 7/2000 | Alferness et al. | |
| 6,110,100 A | 8/2000 | Talpade | |
| 6,123,662 A | 9/2000 | Alferness et al. | |
| 6,125,852 A | 10/2000 | Stevens et al. | |
| 6,162,168 A | 12/2000 | Schweich, Jr. et al. | |
| 6,165,119 A | 12/2000 | Schweich, Jr. et al. | |
| 6,165,120 A | 12/2000 | Schweich, Jr. et al. | |
| 6,179,791 B1 | 1/2001 | Krueger | |
| 6,183,411 B1 | 2/2001 | Mortier et al. | |
| 6,214,047 B1 | 4/2001 | Melvin | |
| 6,260,552 B1 | 7/2001 | Mortier et al. | |
| 6,261,222 B1 | 7/2001 | Schweich, Jr. et al. | |
| 6,264,602 B1 | 7/2001 | Mortier et al. | |
| 6,293,906 B1 | 9/2001 | Vanden Hoek et al. | |
| 6,319,231 B1 | 11/2001 | Andrulitis | |
| 6,324,430 B1 | 11/2001 | Zarinetchi et al. | |
| 6,324,431 B1 | 11/2001 | Zarinetchi et al. | |
| 6,332,863 B1 | 12/2001 | Schweich, Jr. et al. | |
| 6,332,864 B1 | 12/2001 | Schweich, Jr. et al. | |
| 6,332,893 B1 | 12/2001 | Mortier et al. | |
| 6,592,619 B1 * | 7/2003 | Melvin | 623/3.11 |
| 2001/0016675 A1 | 8/2001 | Mortier et al. | |
| 2002/0007216 A1 | 1/2002 | Melvin | |
| 2003/0023132 A1 | 1/2003 | Melvin et al. | |

FOREIGN PATENT DOCUMENTS

| | | |
|---|---|---|
| EP | 0583012 | 2/1988 |
| WO | WO 98/29041 | 7/1998 |
| WO | WO 99/30647 | 6/1999 |
| WO | WO 99/53977 | 10/1999 |
| WO | WO 00/02500 | 1/2000 |
| WO | WO 00/06026 | 2/2000 |
| WO | WO 00/06028 | 2/2000 |
| WO | WO 00/16700 | 3/2000 |
| WO | WO 00/18320 | 4/2000 |
| WO | WO 00/47270 | 8/2000 |
| WO | WO01/67985 | 2/2001 |
| WO | WO 01/28455 | 4/2001 |
| WO | WO 01/85061 | 11/2001 |
| WO | WO 01/91667 | 12/2001 |
| WO | WO 01/95830 | 12/2001 |
| WO | WO 01/95831 | 12/2001 |
| WO | WO 01/95832 | 12/2001 |

OTHER PUBLICATIONS

Melvin, D.B., "*Cardiovascular Surgery: Myocardial Preservation, Cardiorespiratory Support I,*", American Heart Assoc. Abstract, Circulation Part II, vol. 68, No. 4; Scientific Sessions for Nurses; 37th Ann. Meeting; Nov. 14-17, 1983.

Melvin, D.; Schima, H.; Losert, U.; Wolner, E., "*Long-Term Ventricular Wall Actuation: Can and Should it be Systematically Explored?*", Artificial Organs, vol. 20, No. 1, 1996.

Melvin, D.B., et al., "*A Physical Analog of the Failing Left Ventricle for In Vitro Studies of Mechanical Wall Actuation*", Artificial Organs, vol. 20, No. 3, 1996.

Melvin, D.B. et al., "*Reduction of Ventricular Wall Tensile Stress by Geometric Remodeling Device*", ASAIO Journal (Abstract), vol. 45, No. 2 p. 166, Mar. 17, 1999.

Melvin, D.B. , "*Device-Induced Ventricular Geometric Remodeling: Appraisal of Critical Issues*", J. of Cardiac Surgery (Accepted for publication), Presented at the 3rd Symposium of the Soc. of Cardiac Volume Reduction, Apr. 9, 2000 in Osaka, Japan.

* cited by examiner

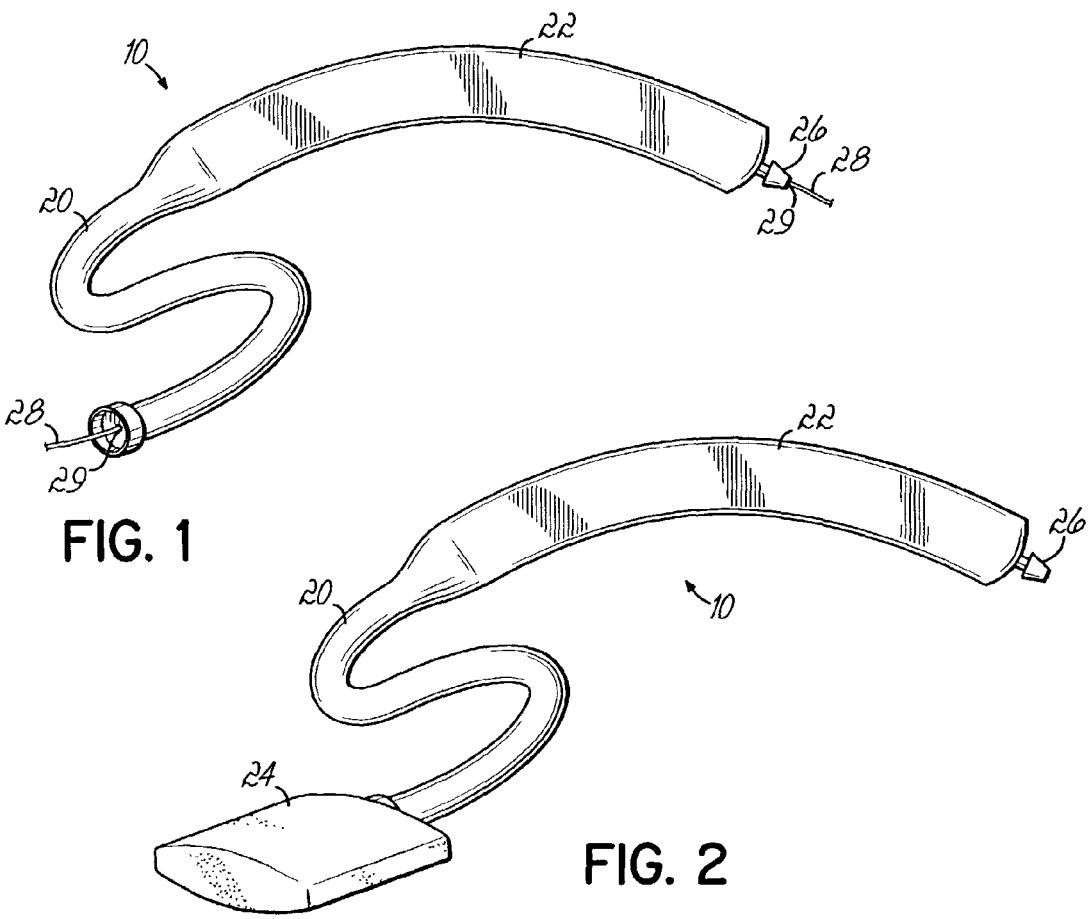
FIG. 1
FIG. 2
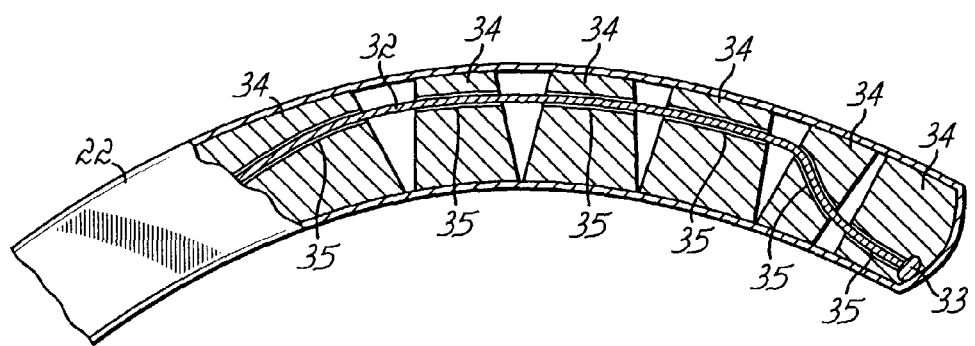
FIG. 1A
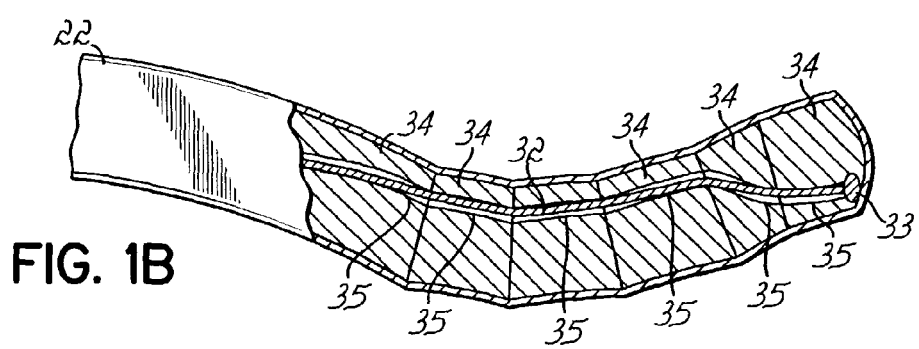
FIG. 1B

MODULAR POWER SYSTEM AND METHOD FOR A HEART WALL ACTUATION SYSTEM FOR THE NATURAL HEART

FIELD OF THE INVENTION

This invention relates generally to assisting the natural heart in operation and, more specifically, to powering a system for actuating a wall of the natural heart.

BACKGROUND OF THE INVENTION

The natural human heart and accompanying circulatory system are critical components of the human body and systematically provide the needed nutrients and oxygen for the body. As such, the proper operation of the circulatory system, and particularly, the proper operation of the heart, are critical in the life, health, and well-being of a person. A physical ailment or condition which compromises the normal and healthy operation of the heart can therefore be particularly critical and may result in a condition which must be medically remedied.

More specifically, the natural heart, or rather the cardiac tissue of the heart, can degrade for various reasons to a point where the heart can no longer provide sufficient circulation of blood for maintaining the health of a patient at a desirable level. In fact, the heart may degrade to the point of failure and thereby may not even be able to sustain life. To address the problem of a failing natural heart, solutions are offered to provide ways in which circulation of blood might be maintained. Some solutions involve replacing the heart. Other solutions are directed to maintaining operation of the existing heart.

One such solution has been to replace the existing natural heart in a patient with an artificial heart or a ventricular assist device. In using artificial hearts and/or assist devices, a particular problem stems from the fact that the materials used for the interior lining of the chambers of an artificial heart are in direct contact with the circulating blood. Such contact may enhance undesirable clotting of the blood, may cause a build-up of calcium, or may otherwise inhibit the blood's normal function. As a result, thromboembolism and hemolysis may occur. Additionally, the lining of an artificial heart or a ventricular assist device can crack, which inhibits performance, even when the crack is at a microscopic level. Such drawbacks have limited use of artificial heart devices to applications having too brief of a time period to provide a real lasting health benefit to the patient.

An alternative procedure also involves replacement of the heart and includes a transplant of a heart from another human or animal into the patient. The transplant procedure requires removing an existing organ (i.e. the natural heart) from the patient for substitution with another organ (i.e. another natural heart) from another human, or potentially, from an animal. Before replacing an existing organ with another, the substitute organ must be "matched" to the recipient, which can be, at best, difficult, time consuming, and expensive to accomplish. Furthermore, even if the transplanted organ matches the recipient, a risk exists that the recipient's body will still reject the transplanted organ and attack it as a foreign object. Moreover, the number of potential donor hearts is far less than the number of patients in need of a natural heart transplant. Although use of animal hearts would lessen the problem of having fewer donors than recipients, there is an enhanced concern with respect to the rejection of the animal heart.

Rather than replacing the patient's heart, other solutions attempt to continue to use the existing heart and associated tissue. In one such solution, attempts have been made to wrap skeletal muscle tissue around the natural heart to use as an auxiliary contraction mechanism so that the heart may pump. As currently used, skeletal muscle cannot alone typically provide sufficient and sustained pumping power for maintaining circulation of blood through the circulatory system of the body. This is especially true for those patients with severe heart failure.

Another system developed for use with an existing heart for sustaining the circulatory function and pumping action of the heart, is an external bypass system, such as a cardiopulmonary (heart-lung) machine. Typically, bypass systems of this type are complex and large, and, as such, are limited to short term use, such as in an operating room during surgery, or when maintaining the circulation of a patient while awaiting receipt of a transplant heart. The size and complexity effectively prohibit use of bypass systems as a long term solution, as they are rarely portable devices. Furthermore, long term use of a heart-lung machine can damage the blood cells and blood borne products, resulting in post surgical complications such as bleeding, thromboembolism, and increased risk of infection.

Still another solution for maintaining the existing natural heart as the pumping device involves enveloping a substantial portion of the natural heart, such as the entire left and right ventricles, with a pumping device for rhythmic compression. That is, the exterior wall surfaces of the heart are contacted and the heart walls are compressed to change the volume of the heart and thereby pump blood out of the chambers. Although somewhat effective as a short term treatment, the pumping device has not been suitable for long term use. Typically, with such compression devices, heart walls are concentrically compressed. The compressive movement patterns, which reduce a chamber's volume and distort the heart walls, may not necessarily facilitate valve closure (which can lead to valve leakage).

Therefore, mechanical pumping of the heart, such as through mechanical compression of the ventricles, must address these issues and concerns in order to establish the efficacy of long term mechanical or mechanically assisted pumping. Specifically, the ventricles must rapidly and passively refill at low physiologic pressures, and the valve functions must be physiologically adequate. The myocardial blood flow of the heart also must not be impaired by the mechanical device. Still further, the left and right ventricle pressure independence must be maintained within the heart.

The present invention addresses the issues of heart wall stiffness and the need for active refilling by assisting in the bending (i.e., indenting, flattening, twisting, etc.) of the heart walls, rather than concentrically compressing the heart walls. Because of the mechanics of deformation in hearts having proportions typical in heart failure (specifically, wall thickness/chamber radius ratios), the deformation from bending and the subsequent refilling of the heart requires significantly less energy than would the re-stretching of a wall that has been shortened to change the chamber volume a similar amount. The present invention facilitates such desirable heart wall bending and specifically protects the heart wall during such bending.

Another major obstacle with long term use of such pumping devices is the deleterious effect of forceful contact of different parts of the living internal heart surface (endocardium), one against another, due to lack of precise control of wall actuation. In certain cases, this coaptation of endocardium tissue is probably necessary for a device that encompasses both ventricles to produce independent output pressures from the left and right ventricles. However, it can compromise the integrity of the living endothelium.

Mechanical ventricular wall actuation has shown promise, despite the issues noted above. As such, devices have been invented for mechanically assisting the pumping function of the heart, and specifically for externally actuating a heart wall, such as a ventricular wall, to assist in such pumping functions.

Specifically, U.S. Pat. No. 5,957,977, which is incorporated herein by reference in its entirety, discloses an actuation system for the natural heart utilizing internal and external support structures. That patent provides an internal and external framework mounted internally and externally with respect to the natural heart, and an actuator device or activator mounted to the framework for providing cyclical forces to deform one or more walls of the heart, such as the left ventricular wall. The invention of U.S. patent application Ser. No. 09/850,554 further adds to the art of U.S. Pat. No. 5,957,977 and that application is incorporated herein by reference in its entirety. The application specifically sets forth various embodiments of activator or actuator devices which are suitable for deforming the heart walls and supplementing and/or providing the pumping function for the natural heart.

For such heart wall activation systems, an actuator device acts on the heart and is coupled to a mechanism necessary for powering or driving the actuator components of the system to mechanically act on the heart wall. The actuator device, driving mechanism and other associated components of the system may be considered to be power systems for the actuation system. The actuator device and other components of the power system involve moving parts which will wear. Therefore, the power system for a heart wall actuation system will generally have to be replaced and exchanged at least once, either due to wear, routine maintenance or malfunction. Since such power systems are interfacing with components positioned near the heart, their replacement and maintenance presents a significant issue to be addressed. Such power systems also must be able to readily interface with the heart or other components of the actuation system for ease of replacement. Furthermore, they should be readily and easily positioned with or inside the body to operate properly in the overall actuation system.

Accordingly, it is an objective of the present invention to provide a device and method for actively assisting the natural human heart in its operation.

It is still another objective of the present invention to provide the necessary actuation of a heart wall to assist the heart at a proper natural rate in a way suitable for long term usage.

It is further an objective to address the maintenance and replacement of components of a heart wall actuation system, particularly the dynamic activation and power components which deliver the actuation forces to the heart.

These objectives and other objectives and advantages of the present invention will be set forth and will become more apparent in the description of the invention below.

SUMMARY OF THE INVENTION

The present invention addresses the above objectives and other objectives and provides an actuation system for assisting the operation of a natural heart. The actuation system includes a framework for interfacing with the natural heart. The framework includes one or more framework elements such as an internal framework element and an external framework element or multiple such internal and external elements. The actuation system also includes a power system configured to be coupled to the framework and configured to engage a heart wall. The power system includes an actuator mechanism for exerting a force on the heart wall. A driving mechanism provides power for actuating the actuator mechanism and a transmission mechanism coupled between the actuator mechanism and the driving mechanism transmits the power to the actuator mechanism. A carrier device contains the actuator mechanism and the transmission mechanism together, generally as a unitary structure so that the power system may be manipulated as a unitary structure. The contained mechanisms are generally stationary with respect to the carrier device. In one embodiment of the invention, the power system is configured to be fixed to the framework.

The transmission mechanism, which may be housed by the carrier device, may be electrical wire, traction cable, torque cable, or hydraulic tubing for example. The power supplied by the driving mechanism may be electrical, mechanical, or hydraulic power. The power of the power system refers to the delivery of an electrical signal or current, delivery of a mechanical motion or delivery of hydraulic fluid, all for the purposes of actuating the actuator mechanism. Therefore, the terms power transmission or power delivery or power supply are not limiting to a particular mode of actuating the actuation mechanism. In one embodiment, the carrier device houses the actuator mechanism and is configured for coupling the actuator mechanism to the framework. The carrier device is elongated and flexible in one embodiment for positioning in the body.

In one embodiment of the invention, the actuator mechanism can include a plurality of juxtaposed elements, such as blocks, which are configured to be drawn together in the actuated state. The juxtaposed elements can cooperate with each other, when drawn together, to assume a predetermined shape or curvature. In another embodiment of the invention, the actuator mechanism may include an inflatable deforming tube structure coupled to a hydraulic fluid supply.

In another embodiment of the invention, the actuation system includes a guide structure for aiding in the placement of the power system in the body. One suitable guide structure is a wire. Another suitable guide structure is a flexible tube.

The present invention, together with other and further objectives thereof, is set forth in greater detail in the following description, taken in conjunction with the accompanying drawings.

BRIEF DESCRIPTION OF THE DRAWINGS

The accompanying drawings which are incorporated in and constitute a part of the specification illustrate embodiments of the invention and, together with a general description of the invention given below, serve to explain the principles of the invention.

FIG. 1 is a perspective view of one embodiment of a power system of the present invention;

FIG. 1A is a sectional view of an embodiment of a suitable actuator mechanism of a power system in the relaxed state;

FIG. 1B is a sectional view of the embodiment of FIG. 1A with the actuator mechanism in the actuated state;

FIG. 2 is a perspective view of an embodiment of a power system of the present invention;

DETAILED DESCRIPTION OF THE INVENTION

Figure 3:
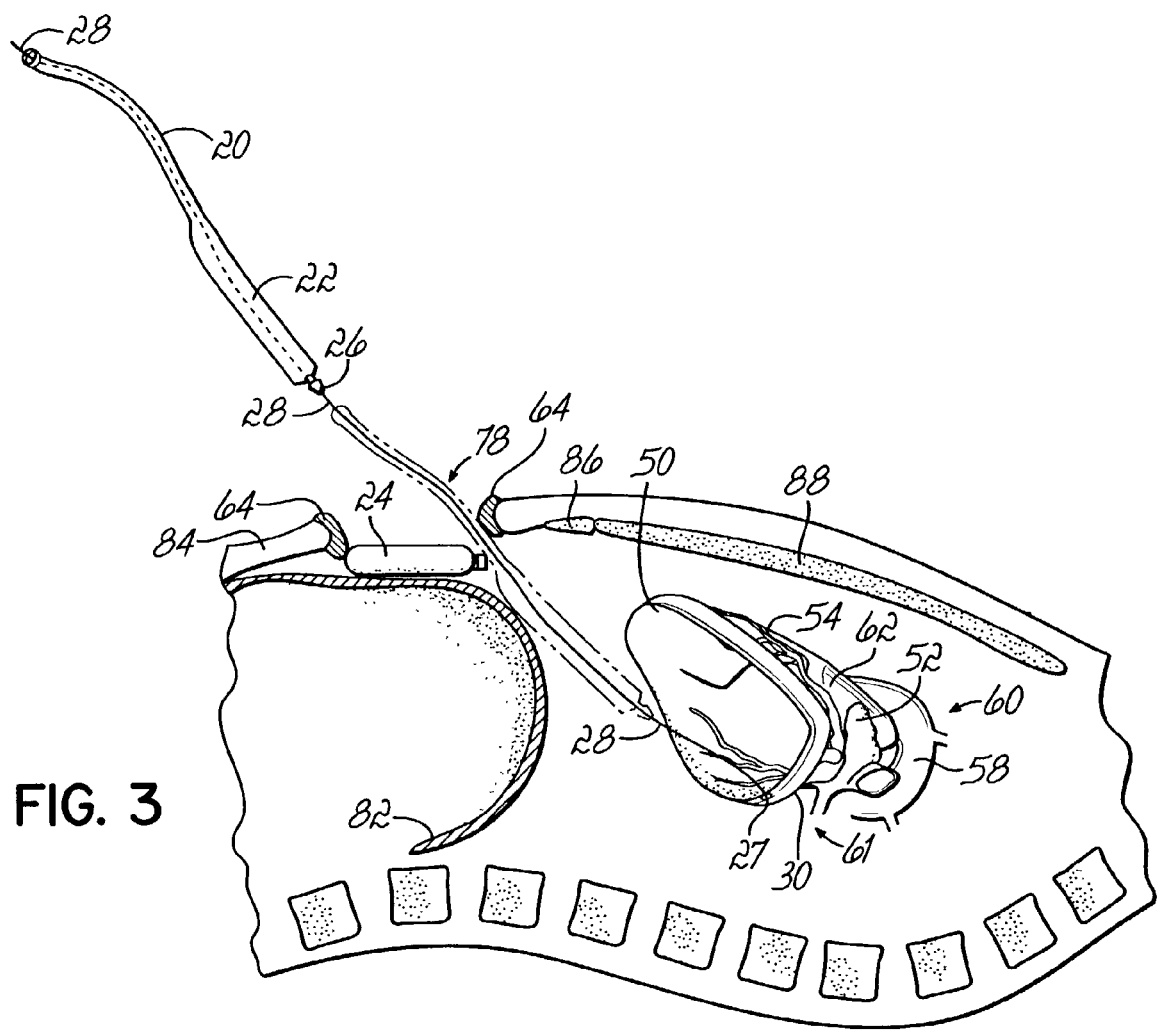
FIG. 3 is a diagram depicting a method of positioning a power system into a patient.

The present invention is directed to an actuation system for assisting the operation of a natural heart. The actuation system disclosed as one example herein comprises a framework for interfacing with the heart, through the wall of the heart, which includes one or more internal framework elements configured to be positioned within the interior volume of the heart and one or more external framework elements configured to be positioned proximate an exterior surface of the heart. A power system is coupled to the framework and configured to engage an exterior surface of the heart. For example, if the left ventricle of the heart is to be actuated utilizing the invention, the external framework can be positioned approximate the exterior left ventricular wall, and the power system will be similarly positioned. This specification discloses a modular power system, which may be exchanged and replaced in a heart wall actuation system as required for repair or for routine maintenance. The modular power system provides a generally unitary structure for positioning and powering the actuator mechanism.

One particular advantage of the present invention is that it provides for simplified replacement of the power and actuator mechanisms which deliver a force or motion to a heart wall to change the volume of a heart chamber. Replacement is done via a limited operation which accesses a driving mechanism or power source near the body surface (e.g. within the abdominal wall) rather than through a major trans-thoracic (open chest) operation to access the heart directly. In one embodiment, the driving mechanism for delivering power to actuate the actuator mechanism can be positioned remotely from the framework, from the heart, and from the actuator mechanism, and can be coupled to the actuator mechanism. In this way, the driving mechanism can be surgically positioned in the body at a site which is readily accessible and particularly more accessible than the chest cavity and the heart. Thus, in this embodiment, the driving mechanism may also be repaired or upgraded without having to perform cardiothoracic surgery on the patient.

The invention operates by coupling a mechanism for exerting a force, that is, an actuator mechanism of the power system, onto an external framework element that has been surgically placed onto the cardiac wall. The actuator mechanism may be selectively and cyclically operated between an actuated state and a relaxed state and may be operable, when in the actuated state, to assume a predetermined shape or curvature and thereby indent a portion of the heart wall to effect a reduction in the volume of the heart and specifically a reduction in one of the chambers of the heart for assisting the heart in its pumping function. The power system includes a driving mechanism for supplying power for actuating the actuator mechanism. The actuator mechanism can be housed in a carrier device, generally at one end, and the driving mechanism can be coupled with the carrier device, generally at the other end. In one embodiment, a transmission mechanism is coupled between the driving mechanism and the actuator mechanism and is housed in the carrier device.

Besides being a conduit of power transmission, the carrier device also serves to help withdraw the power system when being replaced and to advance the new power system when being installed. The invention may also include a guide structure, such as a guide wire or guide tube, as a guidance system for guiding or advancing the power system to its position adjacent to the heart surface.

Figure 5:
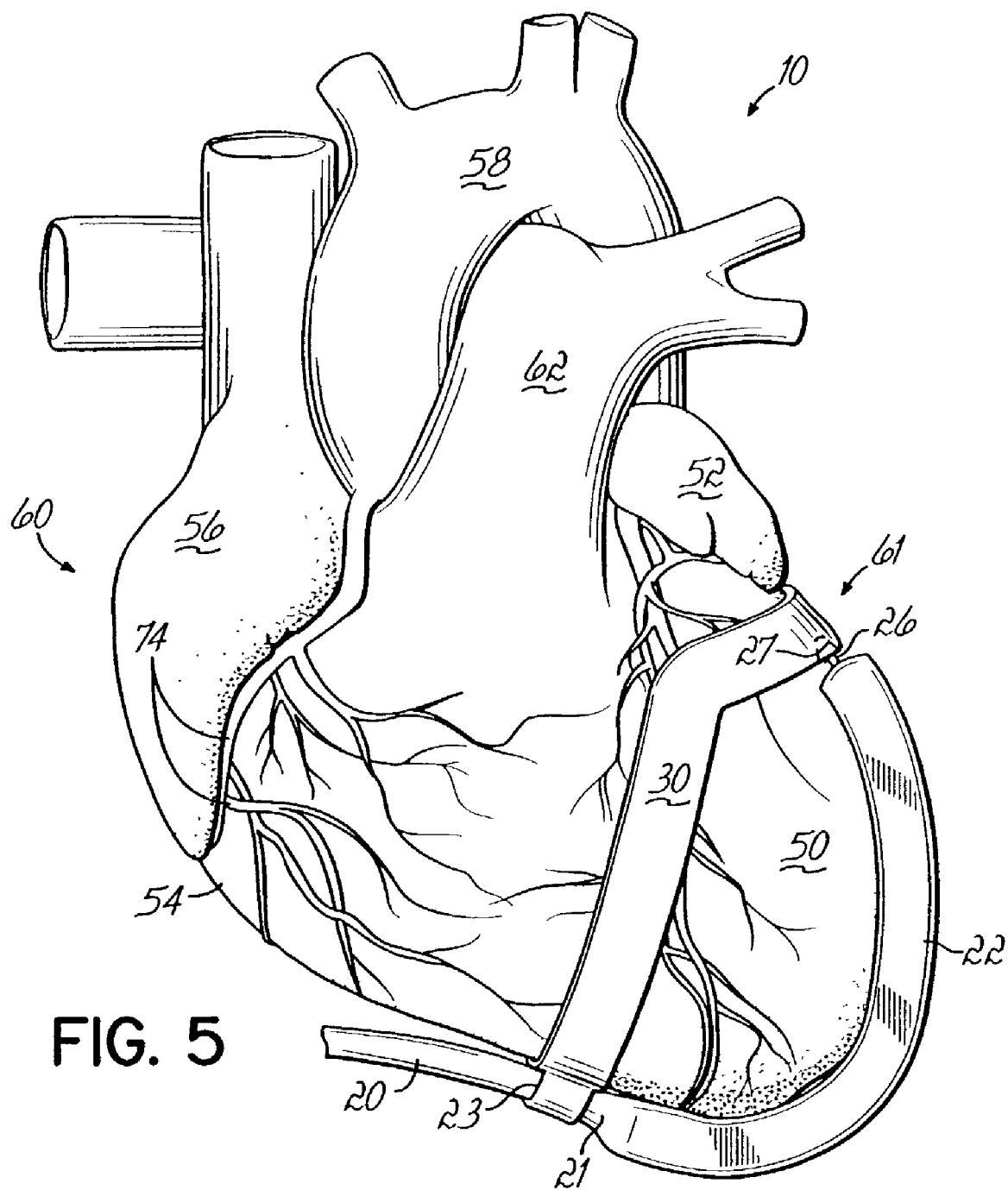
FIG. 5 is a perspective view of the natural heart with the power system coupled to an external framework element.

Referring to FIG. 1, one embodiment of the present invention is shown. Power system 10 includes a force delivery mechanism, or actuator mechanism 22, and a carrier device 20, shown detached from a driving mechanism 24 (FIG. 2). Power system 10 is a modular power system configured for use, in one embodiment, with a framework 61 which interfaces with the heart 60. The power system 10 is configured for engaging a heart wall. Specifically, part or a portion of the power system engages the heart wall. Referring briefly to FIG. 5, an external framework element 30 of the framework 61 is shown coupled to the exterior of heart 60. External framework element 30 is in the form of a yoke and is coupled to internal framework elements (not shown) positioned inside the heart. Greater details of a suitable framework 61 for use with the present invention are set forth in U.S. Pat. No. 5,957,977, which is incorporated herein by reference. While that patent discusses one suitable framework for the modular power system 10 of the invention, it will be understood by a person of ordinary skill in the art that other structures and frameworks will also be suitable for coupling the power system 10 to engage an exterior surface of a heart wall. Furthermore, while the embodiment of the invention illustrated herein is shown coupled to an exterior heart wall surface proximate the left ventricle of the heart, it might as easily be coupled to other areas of the heart for heart wall actuation.

Referring again to FIG. 1, a guide structure, such as a wire 28, is illustrated and is threaded through an elongated passage 29 which passes through a carrier device 20 and through or past the components housed in the carrier device. The guide structure is used as the guidance system for positioning of the actuator mechanism in this embodiment of the invention as discussed further below.

The modular power system 10 illustrated in FIG. 1 generally incorporates an actuator mechanism 22 which is operable, when actuated, for exerting a force on the heart wall surface for the pumping of blood. When the power system 10 engages a heart wall, the actuator mechanism 22 actually engages an outer surface of the heart wall. The actuator mechanism 22 is coupled with the driving mechanism 24 for providing power for actuating the actuator mechanism 22 and contained by the carrier device. A transmission mechanism is coupled with the actuator mechanism 22 for transmitting power to the actuator mechanism 22. In one embodiment, the transmission mechanism is coupled between the actuator mechanism and driving mechanism. Modular power system 10 includes a carrier device 20 coupling the actuator mechanism 22 together with the transmission mechanism. The carrier device may also couple with the driving mechanism 24 to couple the various mechanisms together for providing a generally unitary structure which may be readily and easily manipulated inside the body for maintenance or replacement of the force delivery components of a heart wall actuation system. The carrier device may provide actual mechanical coupling of the various mechanisms and components or, alternatively, may just contain the mechanisms as a housing.

In one embodiment of the present invention, the carrier device 20 is in the form of a generally tubular sleeve which houses the actuator mechanism 22 along with the transmission mechanism. The sleeve may be formed of a biomedically suitable material such as polyurethane or silicon rubber. The carrier device 20 may also be configured for coupling the actuator mechanism 22 to a suitable heart framework 61. For example, as illustrated in FIGS. 1 and 5, and discussed further hereinbelow, the carrier device 20 may include a structure, such as a nipple 26, for coupling the carrier device and actuator mechanism to a suitable framework 61. The other end of the carrier device 20, opposite the actuator mechanism 22, is coupled to a driving mechanism 24 as illustrated in FIG. 2.

FIG. 2 shows an embodiment of a complete power system 10 which includes the actuator mechanism 22, the carrier device 20, and the driving mechanism 24. The driving mechanism 24 is operable for supplying the power for actuating the actuator mechanism 22. To that end, the operation of the driving mechanism 24 and the power it supplies will depend upon the operation of the particular actuation mechanism which is utilized. In accordance with one aspect of the invention, the actuator mechanism 22 may operate electrically, mechanically, or hydraulically, for example. Alternatively, the actuator may utilize a combination of such operational features or may incorporate other operational characteristics. Therefore, the power transmitted to the actuator mechanism to actuate the mechanism may take various forms, including electrical, mechanical, or hydraulic. The term "power" as used herein is not limiting but generally refers to any mechanism or means for actuating the actuator mechanism. The driving mechanism, and the transmission mechanism coupling the driving mechanism to the actuator mechanism for transmitting power thereto, are configured for working with the actuator mechanism. Therefore, the driving mechanism will be configured for providing suitable power or forces to the actuator mechanism and may include a system which is electrical, mechanical, hydraulic, a combination of these or some other suitable system to provide the necessary power. The transmission mechanism may similarly be electrical, mechanical, and/or hydraulic, or a combination of such features for providing the proper interface between the actuator mechanism and carrier device.

The power system 10 depicted in FIG. 2 is configured to be implanted replaceably into a patient from a space outside the chest, such as a space in the subcutaneous tissue, without having to perform cardiothoracic surgery on the patient. The driving mechanism 24, in one embodiment, is detachable and replaceable separately from the carrier device 20. Alternatively, the driving mechanism might be coupled with the carrier device so that the entire system 10 is replaceable as a modular unit.

FIGS. 1A and 1B depict one embodiment of the invention in which actuator mechanism 22 utilizes a plurality of juxtaposed elements, such as articulating blocks 34, for actuating a heart wall. One suitable embodiment of an actuator mechanism 22 is described in U.S. patent application Ser. No. 09/850,554, which is incorporated herein by reference, whereby traction on an actuator cable 32 or other tether or cord effects a change in alignment of the articulating blocks 34 and thus creates a predetermined shape. That is, the blocks 34 are configured to be drawn together in an actuated state and to cooperate with each other, when drawn together, to assume a predetermined shape. The blocks are drawn together when cable 32 is drawn by a force provided by driving mechanism 24. That is, the power associated with the embodiment of FIGS. 1A, 1B is mechanical power and that mechanical power is transmitted to the blocks 34 by cable 32, which acts as the transmission mechanism.

The actuator mechanism 22, when positioned against an exterior surface of a heart wall, moves the heart wall when it takes its predetermined actuated shape and effects a reduction in volume of a chamber of the heart 60, such as the left ventricle 50. This action on the heart wall assists the pumping action of the heart 60. Greater detail of such an actuator mechanism is set forth in U.S. patent application Ser. No. 09/850,554, but FIGS. 1A and 1B show the basic mechanism in relaxed and actuated states, respectively.

The configuration of FIG. 1A depicts the end of cardiac chamber refilling. During filling of the heart chamber, the actuator mechanism 22 is relaxed. As seen in FIG. 1A, a transmission mechanism, in the form of actuator cord 32 is secured at an end 33 inside the actuator mechanism 22 and inside the carrier device 20. For example, the cable might be anchored to an end block by a suitable anchor connection. for example, the cable might be anchored to an end block by a suitable anchor connection. In the embodiment of FIGS. 1A, 1B, the carrier device 20 acts as a casing over the blocks 34 to contain the blocks and form a unitary structure with the transmission mechanism 32. In FIG. 1A, the cable 32 is relaxed and is not drawn so that the blocks 34 are not pulled together at this point in the cardiac cycle. The relaxed actuator mechanism 22 will then generally take the shape of the filling or filled cardiac chamber.

FIG. 1B depicts the configuration of the actuator mechanism imposed in actuation to produce or aid ejection of blood from the cardiac chamber. For ejection of blood, the power system changes the configuration of the actuator blocks 34 by tightening or drawing the actuator cord 32 and pulling or drawing the actuator blocks 34 together to form a predetermined shape to indent or move the heart wall.

The carrier device contains the actuator mechanism and the transmission mechanism in the embodiment of FIGS. 1A, 1B. The cable 32 interfaces with the blocks and passes through passages 35 formed therein. The cable portion away from actuator mechanism 22 may progress generally loosely through carrier device 20. Alternatively, the carrier device has a passage formed therein, similar to the passages 35 in the blocks, for containing the cable so that it may be drawn and relaxed in a controlled manner.

The actuator mechanism 22 is coupled to the driving mechanism 24 through the carrier device 20, which may be flexible. The driving mechanism 24 supplies power (i.e., draws the cable) and the power is transmitted via the actuator cable 32 to draw the blocks together to achieve the predetermined shape of the actuator mechanism 22. The driving mechanism 24 is configured and operable for cyclically drawing and relaxing the cable 32 to effect the shape change of the actuator mechanism to actuate the heart wall. Such an embodiment is an example of a mechanical power system and the driving mechanism provides the mechanical power by drawing the cable. In such an embodiment, driving mechanism 24 may include an electrical power source such as a battery, and other mechanical structure, such as an electromechanical converter, for drawing cable 34. The drawing mechanism may include any suitable mechanism for drawing cable 34, such as a motor, a solenoid, a muscle, etc.

Figure 4:
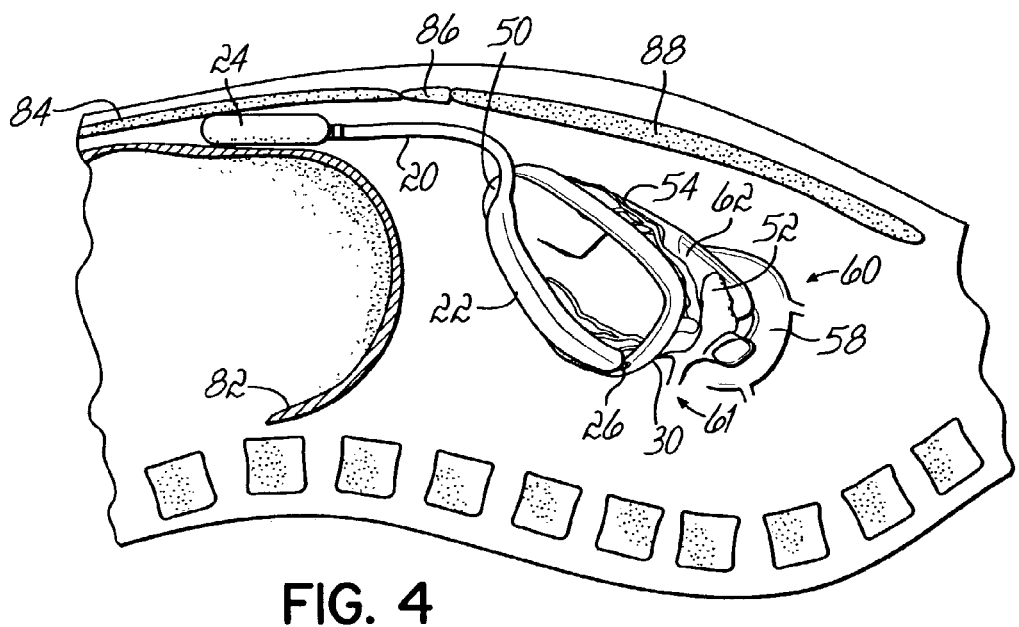
FIG. 4 is a diagram showing the power system of FIG. 3 after positioning inside the body and coupling to a framework element.

FIGS. 3 and 4 show one possible implementation of the invention, showing positioning of the power system 10 near the heart 60 through the abdominal wall 84 of a patient. The power system 10 is configured to operate in conjunction with the framework 61 for providing an actuation system for assisting the operation of a natural heart 60. Generally, the framework 61 is positioned to interface with the heart 60 through cardiothoracic surgery as discussed in U.S. Pat. No. 5,957,977. However, in accordance with one aspect of the present invention, the modular power system 10, which includes an actuator mechanism 22, may be installed in position without such cardiothoracic surgery. Rather, access from a site between the abdominal wall and the overlying skin, or within or deep to the muscular abdominal wall, may be utilized. Therefore, the modular power system 10 of the invention is readily replaceable, such to address maintenance or malfunction. The driving mechanism 24 may already be positioned between skin and muscular fascia of the abdominal wall, as illustrated in FIGS. 3 and 4. In such a case, the carrier device 20, actuator mechanism and any transmission mechanism which is housed in the carrier device would then be selectively uncoupled and coupled with the driving mechanism 24 during installation of the system or during removal and replacement. Alternatively, the entire power system 10, including the driving mechanism 24, might be installed as illustrated in FIGS. 3 and 4.

In this embodiment the surgeon accesses the heart 60 from a position that is posterior to the xyphoid process 86 of the sternum 88 but anterior to the diaphragm 82. The embodiment of FIGS. 3 and 4 uses a guide wire 28 as the guide structure, but other guide structures and systems might be utilized as well. The guide wire 28 is initially coupled to the framework 61, such as to a yoke element 30. The power system, and particularly the carrier device which contains and/or couples together the actuator mechanism and the transmission mechanism, is configured to glide on wire 28 for positioning. In one embodiment, the carrier device 20 includes an elongated passage 29 (see FIG. 1) and the wire slides through the passage. More specifically, the power system is guided into positions along wire 28. The carrier device 20 and the actuator mechanism 22 are advanced between surgical retractors 64 that hold open the surgical incision. The modular system, including the actuator mechanism and any associated transmission mechanism may be readily positioned and manipulated with respect to the remotely located heart. The power system 10 readily and relatively easily slides into working position over the guide wire 28. In this embodiment, the actuator mechanism 22 is effectively coupled to or includes a locking device or structure 26 such as a nipple. In one embodiment, the nipple or other structure 26 is configured as part of the carrier device. This nipple 26 interacts with a mating component 27, such as an opening or some other structure present on the external framework element 30, which is interfaced with the heart 60 as discussed further below. As illustrated in phantom by reference numeral 78, the modular carrier device 20 and actuator mechanism 22 depicted in FIG. 3 illustrate how the modular power system assembly is advanced into working position as it slides over the guide wire 28. As shown in FIG. 1, the cross-sectional size and shape of the actuator mechanism 22 may differ moderately from that of the carrier device 20 when a guide wire 28 is used as the guide structure, because the tube of encapsulating scar tissue that will form after the power system has been implanted can be somewhat elastic to allow the power system to be removed and replaced.

FIG. 4 illustrates the carrier device 20 and the actuator mechanism 22 completely advanced into working position and coupled with the framework element 30. The surgical incision through the abdominal wall 84 is closed, and the driving mechanism 24 rests near the diaphragm 82. The driving mechanism 24 is attached to the carrier device and coupled to the appropriate transmission mechanism, such as a cable 32. In this embodiment, the framework interfaces with the left ventricle 50 of the heart 60.

In addition to the upper abdominal surface depicted in FIGS. 3 and 4, the upper chest, below the clavicle, is another non-limiting example of a site for superficial body access. Pathways can be between the clavicle and upper ribs and over the top surface of the clavicle or sternum or between ribs or through the bed of one or more resected ribs, in addition to the illustrated pathway below the lower rib margin.

FIG. 5 is a more detailed view of a heart 60 with a framework 61 fixed to it to enable use of the replaceable modular power system 10 of the invention. In this embodiment, the framework is also fixed adjacent the exterior wall of the left ventricle 50. Such a framework and the power system 10 of the invention alternatively may be fixed to another section or the wall of the heart or to multiple sections of walls of the heart. This embodiment illustrated includes a nipple 26 coupled to the actuator mechanism 22 of the power system 10, such as with part of the carrier device 20. The nipple is shown, in one form, as being formed as part of carrier device 20, but that is not necessary. The nipple is fixed to a corresponding opening or mating component 27 on the external framework element 30. The nipple 26 couples or locks into place with a portion of the framework when the power system 10 is positioned in place with framework 61 to provide an anchor point for the actuator mechanism. For example, the nipple might be snapped into an aperture 27. As will be understood by a person of ordinary skill in the art, this example of a mating component is intended to be non-limiting. Other mating components or structures may include those which are engaged or released by traction or torsion on a cable designed for such a purpose. Another example is a screw-in fixation system. Numerous other possibilities will be obvious to those ordinarily skilled in the art for anchoring remotely accessible devices for various medical or non-medical applications.

In accordance with another aspect of the present invention, the actuator mechanism may be coupled to the framework in other positions for securing the actuator mechanism to actuate a wall of the heart. Particularly, FIGS. 3 and 4 disclose the actuator mechanism coupled at the proximal end to framework element 30 through nipple 26 and the mating component 27. As alternatively illustrated in FIG. 5, a distal end 21 of the actuator mechanism 22 may also be coupled to another point on the framework element 30. As illustrated in FIG. 5, the carrier device 20 and actuator mechanism 22 may be positioned so that the distal end 21 of actuator mechanism 22 passes through an aperture 23 formed in the framework element 30. In that way, the distal end 21 is further secured to secure the actuator mechanism 22. Alternatively, distal end 21 of the actuator mechanism 22 might otherwise interface with the framework. For example, another nipple and mating component might be utilized similar to the elements 26 and 27, to couple the distal end 21 of the actuator mechanism with the framework element 30.

FIG. 5 also depicts in greater detail the natural heart 60 incorporating a heart wall actuation system in accordance with an embodiment of the invention. Heart 60 includes a lower portion comprising two chambers, namely a left ventricle 50 and a right ventricle 54 which function primarily to supply the main force that propels blood through the circulatory system. The heart 60 also is composed of coronary arteries 74 as well as an upper portion having two chambers, a left atrium 52 and a right atrium 56 which primarily serve as an entryway to the ventricles and assist in moving blood into the ventricles. Generally, the ventricles are in fluid communication with the atria via an atrioventricular valve. More specifically, the left ventricle 50 is in fluid communication with the left atrium 52 through the mitral valve, while the right ventricle 54 is in fluid communication with the right atrium 56 through the tricuspid valve. Generally, the ventricles are in fluid communication with the circulatory system (i.e., the pulmonary and peripheral circulatory system), through semi-lunar valves. More specifically, the left ventricle 50 is in fluid communication with the aorta 58 of the peripheral circulatory system through the aortic valve while the right ventricle 54 is in fluid communication with the pulmonary artery 62 of the pulmonary circulatory system through the pulmonic valve.

Figure 6:
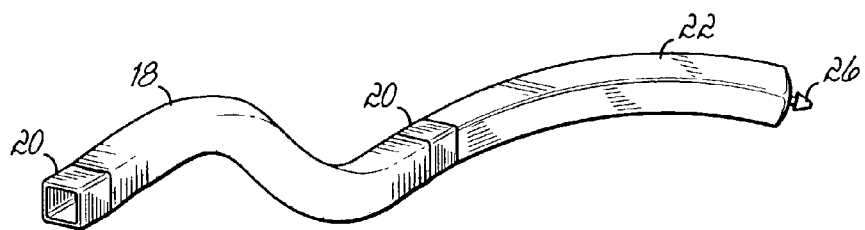
FIG. 6 is a perspective view of an embodiment of the invention with an alternative guide structure.

Now referring to FIG. 6, an alternative embodiment of the invention utilizes a guide structure in the form of a guide tube 18 of a suitable prosthetic material. Rather than sliding along a guide wire as discussed above, the carrier device 20 and actuator mechanism 22 (with the transmission mechanism housed in the carrier device) are passed through the guide tube 18 when positioning components of the power system proximate a heart. In accordance with one aspect of the invention, The guide tube 18 is left in position in the body when the power system components are removed and replaced, thereby leaving a passage for guiding the carrier device 20 and actuator mechanism 22 into position. In one embodiment, the guide tube is a flexible tube through which the power system will pass to be positioned in the proper place with respect to a heart to be actuated. However, effective elasticity of such guide tubes 18 may not be sufficient to allow substantial deformation in cross section, particularly after extended periods of implantation. Therefore, in one embodiment, the cross-sectional profile of tube 18 will need to be generally similar to the carrier devices and actuator mechanisms which are used with these types of tubular guide structures so that the carrier (with enclosed transmission and actuator units) can slide freely through the guide structure. With the guide structure 18 in place, the modular power system 10 of the invention may be readily placed in position, removed, repaired or replaced, and again placed in position, with minimal disruption to the body.

Figure 7:
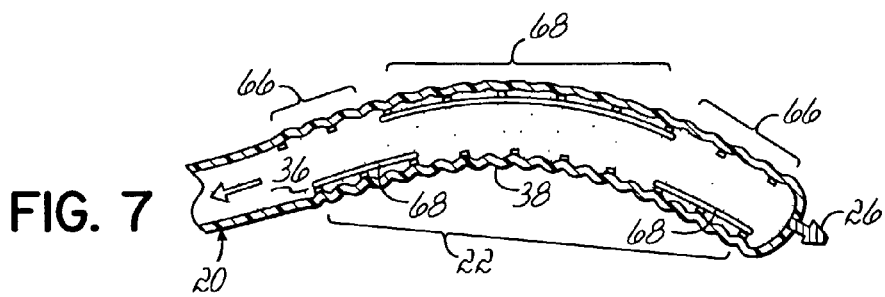
FIG. 7 is a cross-sectional view of another embodiment of an actuator mechanism in the relaxed state.
Figure 8:
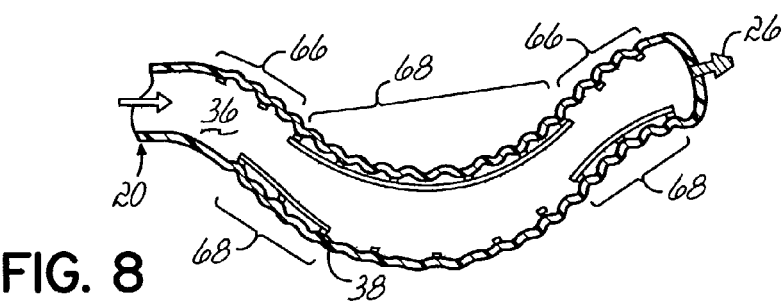
FIG. 8 is a cross-sectional view of the embodiment of FIG. 7 with the actuator mechanism in the actuated state.

FIGS. 7 and 8 show an alternative embodiment of an actuator mechanism 22 as a force delivery system in the form of an inflatable and deformable tube structure, such as a corrugated tube 38 having alternating regions of tethered regions 68 and non-tethered regions 66, or tethered regions of different flexibility. The hydraulic tube 38 has multiple corrugations and can be expanded, and thereby shaped, by the injection of hydraulic fluid 36 into the tubing. In such a case, the hydraulic fluid may be provided by the driving mechanism 24, which may include a source of such fluid. The transmission mechanism may be in the form of an elongated tube or hose to deliver the fluid to the inflatable hydraulic tube 38. For example, the carrier device 20 might be configured to form such an elongated hose. Alternatively, as discussed below, a separate hose 37 might extend inside the carrier device. In another alternative embodiment, the carrier device might form both the actuator mechanism 38 and the tube or hose to deliver hydraulic or other fluid. That is, the actuator mechanism and transmission mechanism might be simply different sections of a unitary tubular structure. As such, the invention does not require that the actuator mechanism, transmission mechanism, and carrier device all be separate pieces. Expansion of and the delivery of the fluid 36 to tube 38 flexibly extends non-tethered or less tethered corrugated regions 66 of the tube wall by pressure produced by an influx of the fluid 36. The tethered or more tethered corrugated regions 68 of the tube wall are generally extended less than regions 66. The non-tethered or less tethered regions 66 cooperate with the tethered regions or more tethered regions 68 to make tube 38 assume a predetermined shape when the hydraulic fluid 36 delivered thereto.

Alternatively, the regions described and illustrated as "untethered" or "less tethered" may also, in fact, be tethered, but tethered at a limiting length that is greater relative to passive length than is the limiting length of those regions described as "tethered." For example, one of the tethered regions may allow a 20% expansion, while an opposite tethered region might allow expansion by only 0–5% to provide controlled curvature. In that way, the greatest resulting curvature may be controlled.

In particular, FIG. 7 depicts the shape or configuration of hydraulic tube 38 assumed during the relaxed state of the actuator mechanism 22, at the end of cardiac chamber filling. The pressure or amount of hydraulic fluid 36 in the tube (shown formed as carrier device 20) is not sufficient to deform it and actuate it such that it significantly acts on the heart. FIG. 8 depicts the shape or configuration assumed by the actuator mechanism 22 in the actuated state to produce or aid ejection of blood from the cardiac chamber. During filling of the heart chamber, the actuator mechanism 22 is relaxed and has a configuration of that in FIG. 7. During ejection of blood, the system is actuated and tube 38 changes configuration from that in FIG. 7 to that in FIG. 8. This actuation or change of configuration of the actuator mechanism 22 can be affected by the delivery of hydraulic fluid 36 which is directed into and out of the actuator mechanism 22 through a suitable transmission mechanism, such as a tube formed by the carrier device 20 or a separate hydraulic hose, such as a hose 37 shown in FIG. 9.

Figure 9:
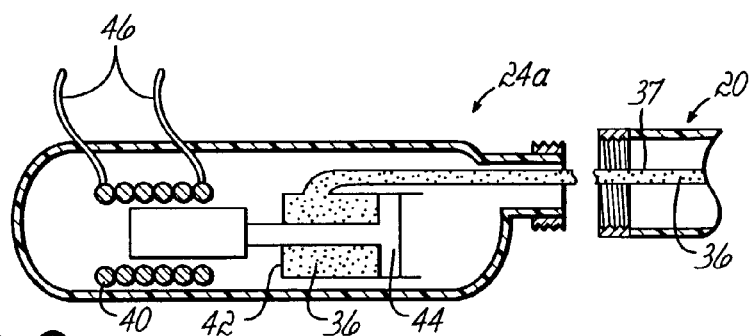
FIG. 9 is a cross-sectional view depicting a driving mechanism embodiment for the present invention.

FIG. 9 is a non-limiting example of a driving mechanism 24a which may be used with the actuator mechanism 22 illustrated in FIGS. 7 and 8. Specifically, the mechanism in 24a includes a hydraulic cylinder 42 containing a piston 44 driven by a solenoid 40 that is, in turn, driven by an electric current delivered by electrical wires 46 or an induction system. Piston 44 might also be driven by an electric motor or other suitable device. In this embodiment, the driving mechanism 24a is operable, in response to signals on electrical wires 46, to drive piston 44 and pump hydraulic fluid 36, or other suitable fluid, through hose 37 to actuate the tube 38 embodiment of the actuator mechanism 22 depicted in FIGS. 7 and 8. As shown in FIG. 9, the transmission mechanism is a hose 37 which passes through the elongated carrier device 20.

Figure 10:
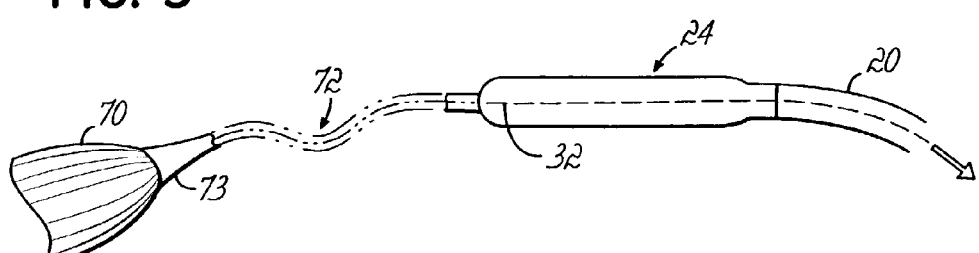
FIG. 10 is a schematic diagram showing a skeletal muscle as a driving mechanism component of one embodiment of the power system.

FIG. 10 illustrates another embodiment of a system employing a skeletal muscle 70 coupled to a prosthetic cable 72 by an appropriate coupling 73 as part of the driving mechanism. For example, an appropriate coupling, such as that described in U.S. Pat. No. 6,214,047, and pending application Ser. No. 09/889,195, may be utilized. That patent and pending application are incorporated herein by reference in their entireties. The prosthetic cable 72 couples to the driving mechanism 24 to provide power for actuation of the actuator mechanism 22. In one example, the driving mechanism 24 may be configured to drive or draw an actuator cable 32 for shaping the blocks 34 of the embodiment of the actuator mechanism 22 depicted in FIG. 1 in response to action by muscle 70. As such, the driving mechanism 24 may include a structure for operably coupling the actuator cable 32 with cable 72 leading from a muscle or muscle group. The driving mechanism, alternatively, may include, levers, ratchets, gears, or other mechanical members which alternatively engage a series of sequentially contracting muscles, to alter the force/displacement ratio of the muscle, or to alter the time for which force is maintained. In the embodiment of FIG. 10, the power source associated with driving mechanism 24 is a muscle or muscles of the human body.

Note that the described embodiments of driving mechanisms, actuating mechanisms and transmission mechanisms are only examples of the way in which various driving mechanisms may drive various force delivery systems or actuator mechanisms in a modular design. Among many feasible alternative combinations, the muscle power source may be adapted to provide hydraulic power transmission to an actuator mechanism. Alternatively, an electric power source (either motor or solenoid) may be adapted to traction a cable for power transmission to the actuator mechanism.

As noted above, one advantage of the present invention is that the modular power system may be replaced, either due to observed functional problems or on a routine schedule, via a limited operation accessing the driving mechanism near the body surface (i.e., within the abdominal wall) rather than through a major transthoracic operation to access the heart directly. The invention is an improvement relative to other heart wall actuators whose force delivery components cannot be replaced without replacing the entire system via a major cardiothoracic operation.

Although the figures and the accompanying text for purposes of clarity show only a single linearly configured power system and a single carrier device, the invention may include multiple actuator mechanisms either with their own carrier devices, or alternatively, with multiple actuator systems coupled with a common carrier device. Furthermore, one or more power systems and carrier devices may be associated only with a single actuator mechanism.

While the present invention has been illustrated by the description of the embodiments thereof, and while the embodiments have been described in considerable detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the spirit or scope of applicant's general inventive concept.

What is claimed is:

1. An actuation system for assisting the operation of a natural heart, the actuation system comprising:
   a framework for interfacing with the heart;
   a power system configured for coupling to the framework for engaging a heart wall, the power system comprising:
      an actuator mechanism operable, when actuated, for exerting a force on a heart wall surface;
      a transmission mechanism coupled with the actuator mechanism for transmitting power to the actuator mechanism to actuate the mechanism; and
      a carrier device coupling the actuator mechanism and the transmission mechanism together, the carrier device housing the actuator mechanism and the transmission mechanism.

2. The actuation system of claim 1, wherein the power system further comprises a driving mechanism for supplying the power to actuate the actuator mechanism.

3. The actuation system of claim 2, wherein the driving mechanism is operable for selectively moving the actuator mechanism between relaxed and actuated states to achieve the desired assistance of the heart.

4. The actuation system of claim 2, wherein the driving mechanism comprises a skeletal muscle, and the transmission mechanism comprises a cable, the skeletal muscle coupled to the cable for actuating the actuator mechanism.

5. The actuation system of claim 1, wherein the carrier device is configured for coupling the actuator mechanism to the framework.

6. The actuation system of claim 5, wherein the carrier device is configured for coupling the actuator mechanism to the framework at a plurality of positions on the framework.

7. The actuation system of claim 1, wherein the framework includes an internal framework element configured to be positioned within the interior volume of the heart and an external framework element configured to be positioned proximate an exterior surface of the heart wall, the internal and external framework elements being coupled together.

8. The actuation system of claim 1, wherein the actuator mechanism is operable, when in the actuated state, to assume a predetermined shape and thereby indent a portion of the heart wall to effect a reduction in the volume of the heart.

9. The actuation system of claim 8, wherein the actuator mechanism includes a plurality of juxtaposed elements, the elements configured to be drawn together in the actuated state and to cooperate with each other, when drawn together, to assume the predetermined shape.

10. The actuation system of claim 9, wherein the elements are blocks coupled together by an actuator cable, the actuator cable being operably coupled to draw the blocks together and form the predetermined shape.

11. The actuation system of claim 8, wherein the actuator mechanism includes a deformable tube structure, the transmission mechanism configured for delivering fluid to the deformable tube structure for forming the tube into the predetermined shape.

12. The actuation system of claim 11, wherein the deformable tube structure includes tethered regions, at least one of the tethered regions having a limited length which is greater than a limited length of another tethered region so that one tethered region may be extended more than another tethered region to form the tube into the predetermined shape.

13. The actuation system of claim 11, wherein the deformable tube structure includes tethered regions and non-tethered regions, the non-tethered regions being operably extended by introducing fluid, to cooperate with the tethered regions to form the tube into the predetermined shape.

14. The actuation system of claim 11, further comprising a driving mechanism comprising a cylinder for driving fluid to the deformable tube structure for forming the tube into the predetermined shape.

15. The actuation system of claim 1, wherein the power system is configured for being coupled with the framework.

16. The actuation system of claim 1, wherein the carrier device is elongated and flexible.

17. The actuation system of claim 1, wherein the transmission mechanism is one of electrical, mechanical, and hydraulic.

18. The actuation system of claim 1, further comprising a guide structure for aiding in the placement of the power system in the body, the guide structure configured for being coupled with the carrier device for positioning the power system in the body.

19. The actuation system of claim 18, wherein the guide structure comprises a wire, the carrier device being configured to slide along the wire.

20. The actuation system of claim 19, the carrier device including an elongated passage therethrough, the wire sliding through the passage for placement of the power system.

21. The actuation system of claim 18, wherein the guide structure comprises a guide tube, the actuator mechanism configured to slide through the tube for placement of the power system.

22. An actuation system for assisting the operation of a natural heart, the actuation system comprising:
a power system configured for positioning proximate a heart wall and including an actuator mechanism which is operable, when actuated, for exerting a force on a heart wall surface;
a transmission mechanism coupled with the actuator mechanism for transmitting power to the actuator mechanism to actuate the mechanism;
a guide structure coupled with the power system for aiding in the placement of the power system in the body, the guide structure configured for guiding the power system from a position remote from the heart to proximate the heart wall;
a carrier device housing the actuator mechanism and configured for securing the actuator mechanism to a framework proximate the heart wall once it is guided to that position.

23. The actuation system of claim 22, wherein the guide structure comprises a wire, at least a portion of the power system being configured to slide along the wire.

24. The actuation system of claim 23, the power system portion including an elongated passage therethrough, the wire sliding through the passage for placement of the power system.

25. The actuation system of claim 22 wherein the carrier device couples the actuator mechanism and the transmission mechanism together.

26. The actuation system of claim 22 wherein said carrier device is coupled with the guide structure for aiding in the placement of the power system in the body.

27. The actuation system of claim 22 wherein the carrier device is coupled with the guide structure for aiding in the placement of the power system in the body.

28. The actuation system of claim 27, wherein the carrier device is elongated and flexible.

29. The actuation system of claim 22 further comprising a framework for interfacing with the heart, the guide structure being coupled to the framework.

30. The actuation system of claim 22 wherein the power system comprises a unitary structure, including the actuator mechanism, for being guided to proximate the heart wall.

* * * * *